United States Patent [19]

Foster

[11] Patent Number: 4,562,286

[45] Date of Patent: Dec. 31, 1985

[54] PROCESS FOR PREPARING METHOXYTRIFLUOROMETHYLNAPHTHOIC ACID FROM DIMETHYLNAPHTHALENE

[75] Inventor: Arthur M. Foster, Lewiston, N.Y.

[73] Assignee: Occidental Chemical Corporation, Niagara Falls, N.Y.

[21] Appl. No.: 667,183

[22] Filed: Nov. 1, 1984

[51] Int. Cl.[4] ............................................. C07C 63/34
[52] U.S. Cl. .................................. 562/467; 570/127;
570/182; 562/427; 562/444; 562/450; 260/544
B; 560/56; 560/100
[58] Field of Search ......................... 562/467; 560/56;
570/127, 182

[56] References Cited

PUBLICATIONS

Fung et al., Canadian Journal of Chem., vol. 61, pp. 368–371 (1982).

*Primary Examiner*—Paul J. Killos
*Attorney, Agent, or Firm*—James F. Tao; William G. Gosz

[57] ABSTRACT

A multi-step process is described for preparing a methoxytrifluoromethylnaphthoic acid compound of formula

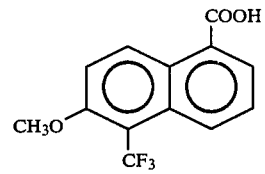

from 1,5-dimethylnaphthalene and for preparing novel intermediate compounds of formula

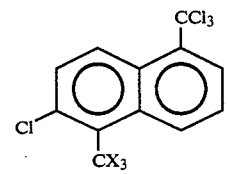

where X is chlorine or fluorine.

Methoxytrifluoromethylnaphthoic acid is useful for preparing biologically active compounds such as naphthyl thioamide derivatives which inhibit aldose reductase activity.

12 Claims, No Drawings

PROCESS FOR PREPARING METHOXYTRIFLUOROMETHYLNAPHTHOIC ACID FROM DIMETHYLNAPHTHALENE

BACKGROUND OF THE INVENTION

This invention relates to a novel process and intermediates for preparing a methoxytrifluoromethylnaphthoic acid compound of formula

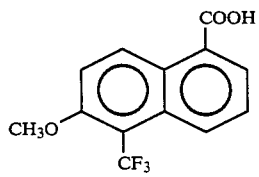

from 1,5-dimethylnaphthalene. The methoxytrifluoromethylnaphthoic acid compound of the present invention, which is designated as 2-methoxy-1-trifluoromethyl-5-napthoic acid, is useful as a chemical intermediate for the synthesis of various end-products. In particular, one such end-product is a therapeutic agent having efficacy for inhibiting aldose reductase activity in human tissues. This compound, which is a naphthyl thioamide compound of formula

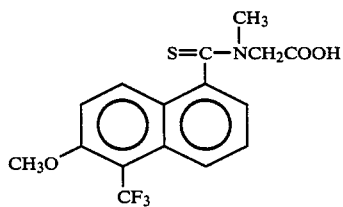

is currently being evaluated for such efficacy. This is a proprietary compound of the Ayerst Research Laboratories and is designated by the trademark Tolrestat. Tolrestat is believed to inhibit the aldose reductase enzyme in human cells which converts glucose into sorbitol. Excessive sorbitol production in humans is a condition common to many by diabetics, and has been linked to chronic complications among diabetics such as blindness, hypertension, pain and discomfort. See *Chemical & Engineering News*, page 5 (Sept. 5, 1983).

The cost of Tolrestat is presently quite high due in part to the high cost of the raw materials used in manufacturing this drug. One of the primary raw materials is the methoxytrifluoromethylnaphthoic acid of the present invention.

Various methods are disclosed in the prior art for preparing 2-methoxy-1-trifluoromethyl-5-naphthoic acid. Thus, it is known to react a mixture of iodine and iodic acid with 6-methoxy-1-naphthalenecarboxylic acid methyl ester in a mixture of acetic acid and sulfuric acid to prepare 5-iodo-6-methoxy-1-naphthalenecarboxylic acid methyl ester. This compound can then be reacted with trifluoromethyl iodide in pyridine in the presence of copper powder and subsequently hydrolyzed in a mixture of sodium hydroxide and methanol to prepare 2-methoxy-1-trifluoromethyl-5-naphthoic acid. Alternatively, the 5-iodo-6-methoxy-1-naphthalenecarboxylic acid methyl ester can be reacted with a mixture of copper, mercuric thiofluoride, and cuprous thiomethyltrifluoride (CuSCF$_3$) in dimethyl-formamide, and subsequently hydrolyzed in a mixture of 2-methoxy- ethanol and sodium hydroxide to prepare the target compound. These procedures are described in more detail in examples 1f, 1h and 63 of European Patent Application 59,596, published Sept. 8, 1982.

Fung et al in the *Canadian Journal of Chemistry*, Vol. 61, pp. 368–371 (1982) describe the preparation of 1-trifluoromethyl-2-naphthalenols from 3-chloropropyltoluene. The 3-chloropropyltoluene is reacted with magnesium, a catalytic amount of iodine and a suspension of lithium trifluoroacetate in anhydrous ether to prepare the corresponding ketone. The ketone is then used to prepare a ketone- oxime by reaction with potassium nitrate in water and acetic acid. The ketone-oxime is then reacted with concentrated sulfuric acid to close the ring, and subsequently hydrolyzed with concentrated hydrochloric acid to prepare the hydroxyketone. The hydroxyketone is dehydrated by reaction with thionyl chloride, 4-dimethylaminopyridine and pyridine, and subsequently methylated with dimethylsulfate to prepare 2-methoxy-5-methyl-1-trifluoromethylnaphthalene, the methyl analog of the carboxylic acid compound of the present invention.

As is evident from the foregoing, prior art processes for preparing methoxytrifluoromethylnaphthoic acid or analogous compounds suffer from numerous disadvantages. These processes are cumbersome, involve expensive reactants and/or reagents and processing techniques, and are not readily adaptable for commerical production. It will be readily apparent to those skilled in the art, therefor, that a need exists to develop an improved process for preparing methoxytrifluoromethylnaphthoic acid using readily available and inexpensive raw materials and commerically feasible processing techniques. One such process utilizing 1-methyl-5-naphthoic acid as a starting material is disclosed in a commonly assigned copending application filed of even date herewith. The present application is directed to an alternate process utilizing 1,5-dimethylnaphthalene as a starting material.

SUMMARY OF THE INVENTION

In accordance with this invention, a process for preparing 2-methoxy-1-trifluoromethyl-5-naphthoic acid from 1,5-dimethylnaphthalene comprises the steps of:

(a) chlorinating 1,5-dimethylnaphthalene in the liquid phase to prepare 2-chloro-1,5-dimethylnaphthalene, (b) photochlorinating the 2-chloro-1,5-dimethylnaphthalene in the liquid phase to prepare 2-chloro-1,5-bis(trichloromethyl)naphthalene, (c) fluorinating the 2-chloro-1,5-bis(trichloromethyl)naphthalene in the liquid phase in the presence of a halogen transfer catalyst to prepare 2-chloro-1-trifluoromethyl-5-trichloromethylnaphthalene, (d) hydrolyzing the 2-chloro-1-trifluoromethyl-5-trichloromethyl naphthalene in the presence of iron or a Lewis Acid catalyst to prepare 2-chloro-1-trifluoromethyl-5-naphthoyl chloride, (e) esterifying the 2-chloro-1-trifluoromethyl-5-naphthoyl acid chloride by reaction with a lower alkanol to prepare 2-chloro-1-trifluoromethyl-5-naphthalate, (f) methoxylating the 2-chloro-1-trifluoromethyl-5-naphthalate by reaction with sodium methoxide in the presence of a cuprous halide to prepare 2-methoxy-1-trifluoromethyl-5-naphthalenecarboxylate, and (g) hydrolyzing the 2-methoxy-1-trifluoromethyl-5-naphthalate.

The intermediate compounds prepared according to steps (b) and (c) are novel intermediate compounds which can be represented by the formula

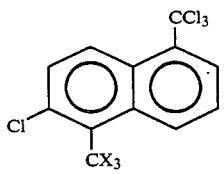

where X is chlorine or fluorine.

DETAILED DESCRIPTION OF THE INVENTION

The process of the present invention is a multi-stage reaction sequence for preparing a methoxytrifluoromethylnaphthoic acid compound of formula

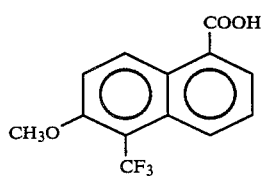

from 1,5-dimethylnaphthalene. The methoxytrifluoromethylnaphthoic acid compound of formula (I) is designated as 2-methoxy-1-trifluoromethyl-5-naphthoic acid in accordance with accepted nomenclature. 1,5-Dimethylnaphthalene is a readily available compound which can be obtained in ordinary channels of commerce.

The first step of the process is the reaction 1,5-dimethylnaphthalene with a suitable chlorinating agent to prepare 2-chloro-1,5-dimethylnaphthalene. This reaction can be illustrated as follows:

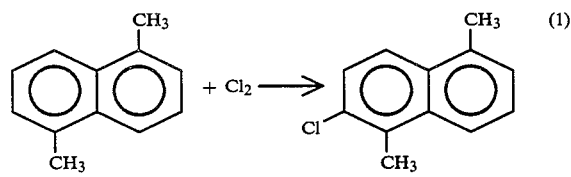

Reaction (1) is conducted in the liquid phase, either neat or in the presence of a solvent. Suitable solvents include halogenated aromatic compounds such as carbon tetrachloride. In a preferred embodiment of this reaction, chlorine is employed as the chlorinating agent and a Lewis acid catalyst, such as antimony pentachloride, is used as a chlorination catalyst. Although other chlorinated isomers will be formed during this reaction, these isomers can be separated using well-known separatory techniques such as distillation and solvent extraction. Temperature and pressure conditions for this reaction are not critical and can vary over wide limits.

The 2-chloro-1,5-dimethylnaphthalene compound is then reacted with chlorine in a photochlorination reaction to chlorinate the methyl groups and prepare 2-chloro-1,5-bis(trichloromethyl)naphthalene in accordance with the following reaction.

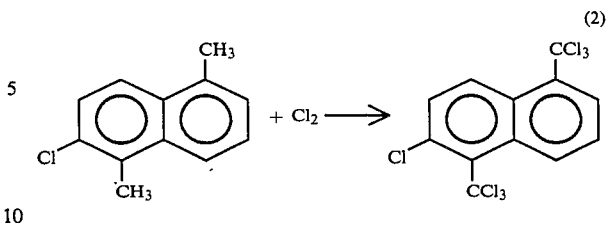

Reaction (2) is a liquid phase photochlorination reaction which is preferably conducted in a halogenated organic solvent such as carbon tetrachloride. Process conditions for this reaction are also not critical and a wide range of temperature and pressure conditions can be used. The product of reaction (2) is a novel compound.

The 2-chloro-1,5-bis(trichloromethyl)naphthalene compound is then reacted with a fluorinating agent in the presence of a halogen transfer catalyst to prepare 2-chloro-1-trifluoromethyl-5-trichloromethylnaphthalene in accordance with the following reaction.

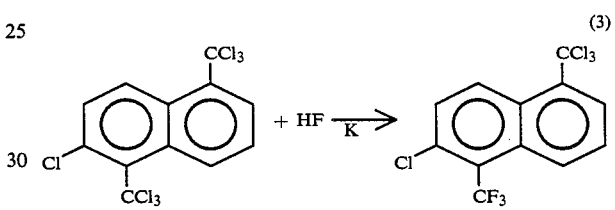

Reaction (3) is also conducted in the liquid phase in the presence of a halogen transfer catalyst. Such catalysts are well-known in the literature and include, for example, ferric chloride, aluminum chloride, titanium tetrachloride, antimony pentafluoride, antimony pentachloride, and the like. The preferred catalyst is antimony pentachloride. The fluorination process can be conducted over a wide range of process conditions and either with or without a solvent. Suitable solvents include DMF, benzene, nitrobenzene, and the like. A preferred fluorinating agent is hydrogen fluoride which is suitably employed in a three molar excess. Other isomers will be produced by this reaction in varying amounts, but these isomers can be separated from the final product using standard separatory techniques. The product of reaction (3) is also a novel compound.

The 2-chloro-1-trifluoromethyl-5-trichloromethylnaphthalene compound is then hydrolyzed in the presence of iron or a Lewis Acid catalyst to prepare 2-chloro-1-trifluoromethyl-5-naphthoyl chloride in accordance with the following reaction.

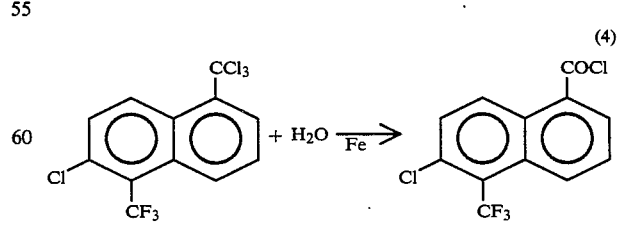

The 2-chloro-1-trifluoromethyl-5-naphthoyl acid chloride is then reacted with a lower alkanol to prepare 2-chloro-1-trifluoromethyl-5-naphthalate as shown below.

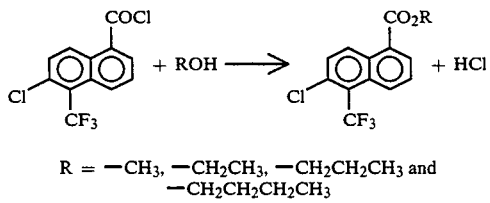 (5)

R = —CH₃, —CH₂CH₃, —CH₂CH₂CH₃ and —CH₂CH₂CH₂CH₃

The lower alkanol employed in the esterification reaction (5) is preferably methanol, although other alkanols such as ethanol, propanol and butanol can also be successfully used in this process. The expression "lower alkanol" is therefore intended to include all of these alcohols.

The 2-chloro-1-trifluoromethyl-5-naphthalate is then reacted with sodium methoxide in the presence of a cuprous halide, preferably cuprous chloride, to prepare 2-methoxy-1-trifluoromethyl-5-naphthalate as shown below.

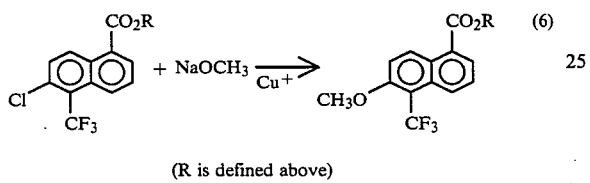 (6)

(R is defined above)

The reaction sequence of this invention is completed upon hydrolyzing the 2-methoxy-1-trifluoromethyl-5-naphthalate as shown below.

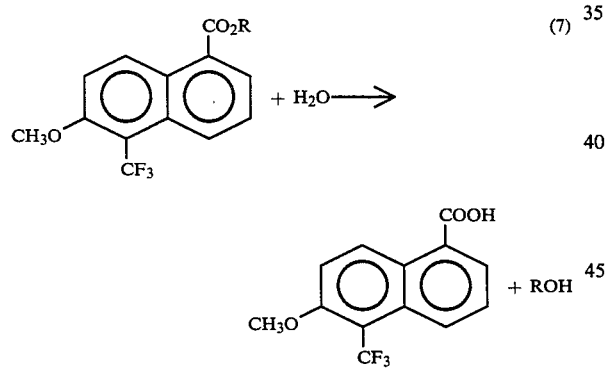 (7)

The final hydrolysis reaction (7) can be either acid or base catalyzed. A base catalyzed reaction can be conducted in an aqueous solution of methanol and an alkali metal hydroxide such as sodium hydroxide or potassium hydroxide.

Methoxytrifluoromethylnaphthoic acid produced according to this process can be further reacted with N-methylglycene to prepare an amidoacid of formula

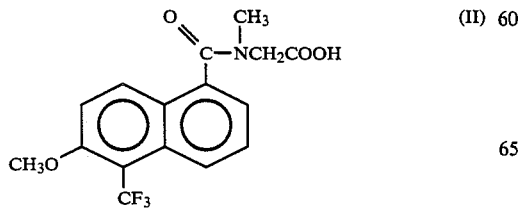 (II)

The amidoacid can be easily converted into a naphthyl thioamide compound of formula

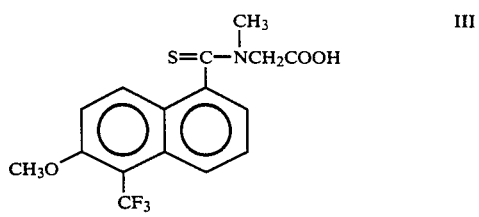 III by reaction with phosphorus pentasulfide. This latter compound III is a useful therapeutic agent for the treatment of diabetic side-effects.

What is claimed is:

1. A process for preparing a methoxytrifluoromethylnaphthoic acid compound of formula

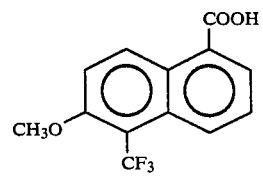

comprising the steps of
(a) chlorinating 1,5-dimethylnaphthalene in the liquid phase to prepare a chlorodimethylnaphthalene of formula

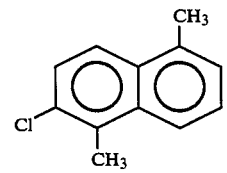

(b) photochlorinating the chlorodimethylnaphthalene of step (a) in the liquid phase to prepare a chloro-bis(trichloromethyl)naphthalene of formula

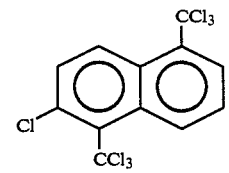

(c) fluorinating the chloro-bis(trichloromethyl)naphthalene of step (b) in the liquid in the presence of a halogen transfer catalyst to prepare a chlorotrifluoromethyltrichloromethylnaphthalene of formula

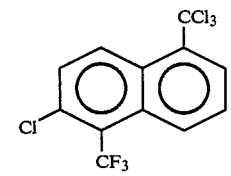

(d) hydrolyzing the chlorotrifluoromethyltrichloromethyl naphthalene of step (c) in the presence of iron or a Lewis Acid catalyst to prepare a chlorotrifluoromethylnaphthoyl acid chloride of formula

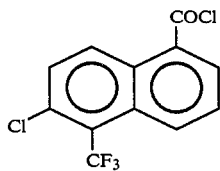

(e) esterifying the chlorotrifluoromethylnaphthoyl acid chloride of step (d) by reaction with a lower alkanol to prepare a chlorotrifluoromethylnaphthalate of formula

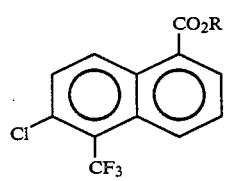

where R is methyl, ethyl, propyl or butyl, (f) methoxylating the chlorotrifluoromethylnaphthalate of step (e) by reaction with sodium methoxide in the presence of a cuprous halide to prepare a methoxytrifluoro methylnaphthalate of formula

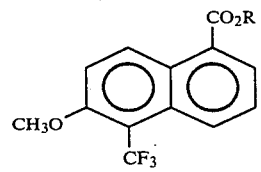

where R is defined in step (e), and (g) hydrolyzing the methoxytrifluoromethylnaphthalate of step (f).

2. The process of claim 1 wherein the chlorination in step (a) is conducted in a solvent.

3. The process of claim 2 wherein the solvent is CCl₄.

4. The process of claim 1 wherein step (a) is conducted in the presence of a catalytic amount of a Lewis acid catalyst.

5. The process of claim 4 wherein the chlorinating agent in step (a) is chlorine and the Lewis acid catalyst is antimony pentachloride.

6. The process of claim 1 wherein the photochlorination in step (b) is conducted in a halogenated solvent.

7. The process of claim 6 wherein the halogenated solvent is CCl₄.

8. The process of claim 1 wherein the fluorinating agent is hydrogen fluoride.

9. The process of claim 8 wherein the halogen transfer catalyst is antimony pentachloride.

10. The process of claim 1 wherein the lower alkanol in step (e) is methanol and the cuprous halide is cuprous chloride.

11. The process of claim 10 wherein the hydrolysis in step (g) is conducted in an aqueous solution of a sodium hydroxide and methanol.

12. A compound of formula

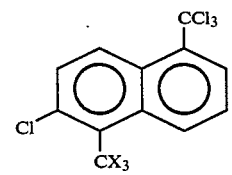

where X is chlorine or fluorine.

* * * * *